US006637055B1

(12) United States Patent
Nanan

(10) Patent No.: US 6,637,055 B1
(45) Date of Patent: Oct. 28, 2003

(54) YOGA INVERSION BED WITH LEG ATTACHMENT

(76) Inventor: Dharamraj Nanan, 1937 Lebanon St., Hyattsville, MD (US) 20783

( * ) Notice: Subject to any disclaimer, the term of this patent is extended or adjusted under 35 U.S.C. 154(b) by 0 days.

(21) Appl. No.: 10/309,902

(22) Filed: Dec. 5, 2002

Related U.S. Application Data

(60) Provisional application No. 60/382,338, filed on May 23, 2002.

(51) Int. Cl.[7] .......................... A61G 7/005; A61H 1/02; A61F 5/045

(52) U.S. Cl. ............................ 5/610; 482/144; 482/145

(58) Field of Search ............................ 5/610, 618, 621, 5/624, 613; 482/143, 144, 145

(56) References Cited

U.S. PATENT DOCUMENTS

| | | | |
|---|---|---|---|
| 3,081,085 | A | 3/1963 | De Girolamo |
| 3,286,708 | A | 11/1966 | Gartner |
| 3,388,700 | A | 6/1968 | Mountz |
| 3,589,358 | A | 6/1971 | Megal |
| 3,593,708 | A | 7/1971 | Steele |
| 3,806,109 | A | 4/1974 | Weber et al. |
| 4,103,681 | A | 8/1978 | Shanley |
| 4,113,250 | A | 9/1978 | Davis |
| 4,232,662 | A | 11/1980 | Barber |
| 4,438,761 | A | 3/1984 | McGowen |
| 4,461,287 | A | 7/1984 | Takahashi |
| 4,672,697 | A | 6/1987 | Schurch |
| 4,690,133 | A | 9/1987 | George |
| 4,739,749 | A | 4/1988 | Lindley |
| 4,913,424 | A | 4/1990 | Pepin |
| 5,002,043 | A | 3/1991 | George |
| 5,133,741 | A | 7/1992 | Filho |
| 5,334,123 | A | 8/1994 | Rutherford |
| 5,416,939 | A | 5/1995 | Maalouli |
| 5,885,197 | A | 3/1999 | Barton |
| 5,935,050 | A | 8/1999 | Shahan |
| 6,030,325 | A | 2/2000 | Ottoson et al. |
| 6,243,897 | B1 | 6/2001 | Sumiya |
| 6,309,330 | B1 | 10/2001 | Thornton |

*Primary Examiner*—Alexander Grosz
(74) *Attorney, Agent, or Firm*—Peter A. Borsari; Eric W. Trucksess

(57) ABSTRACT

A bed which is pivotable from a horizontal arrangement to a vertical arrangement to controllably invert a human body from a supine position to an inverted position. The arrangement of the bed is controlled by at least one electric actuator so that injured or ill persons may attain the inverted position safely and easily. Hanging by their legs, users are suspended in the inverted position by a trapeze bar which is supported within a rotatable leg attachment; by adjusting the position of the trapeze bar and the angle of the leg attachment, selective stimulation may be applied to targeted acupressure points. A heating and/or vibrating unit may be included to provide further stimulation to the spine.

19 Claims, 8 Drawing Sheets

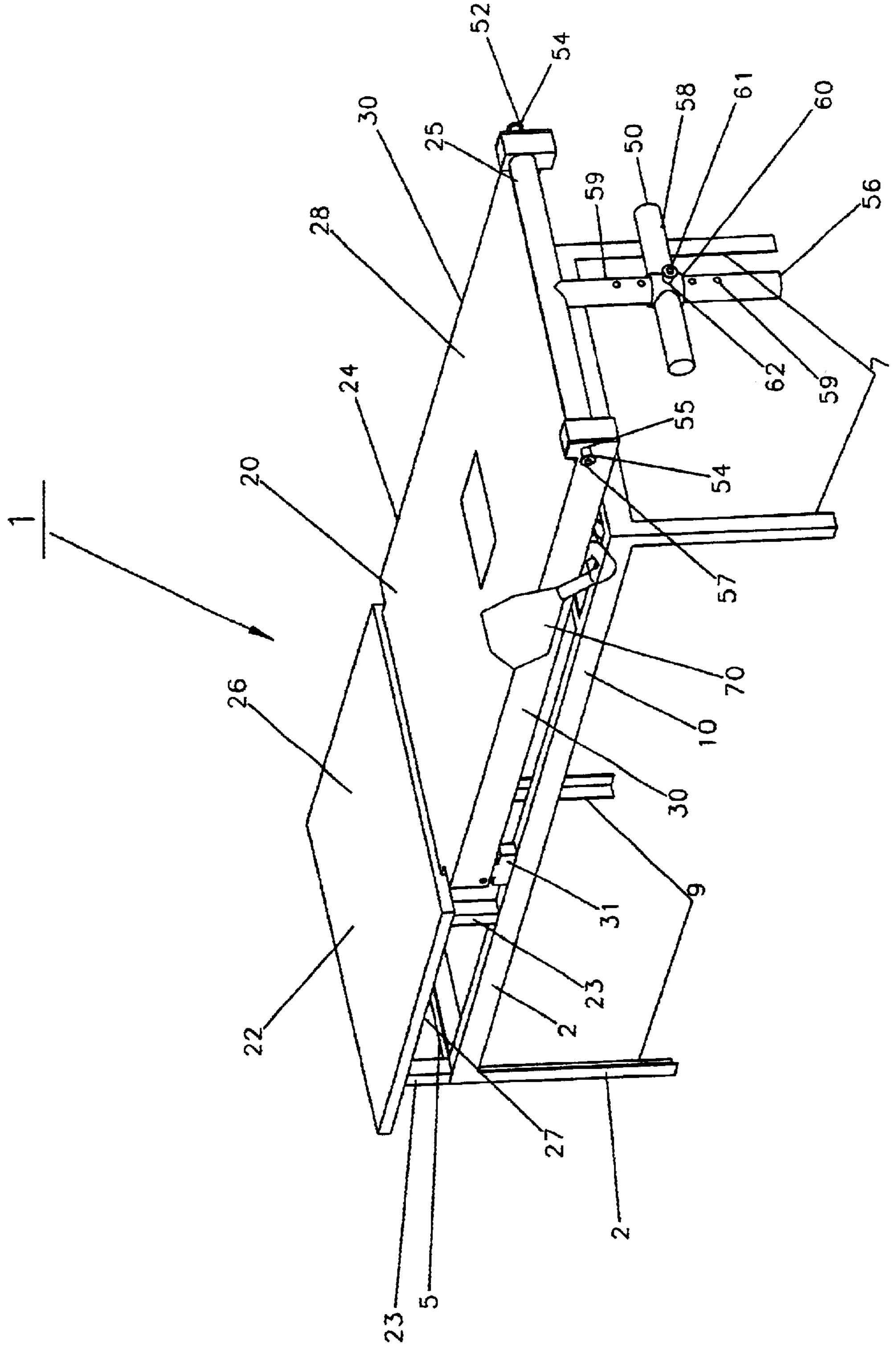
Figure (1)

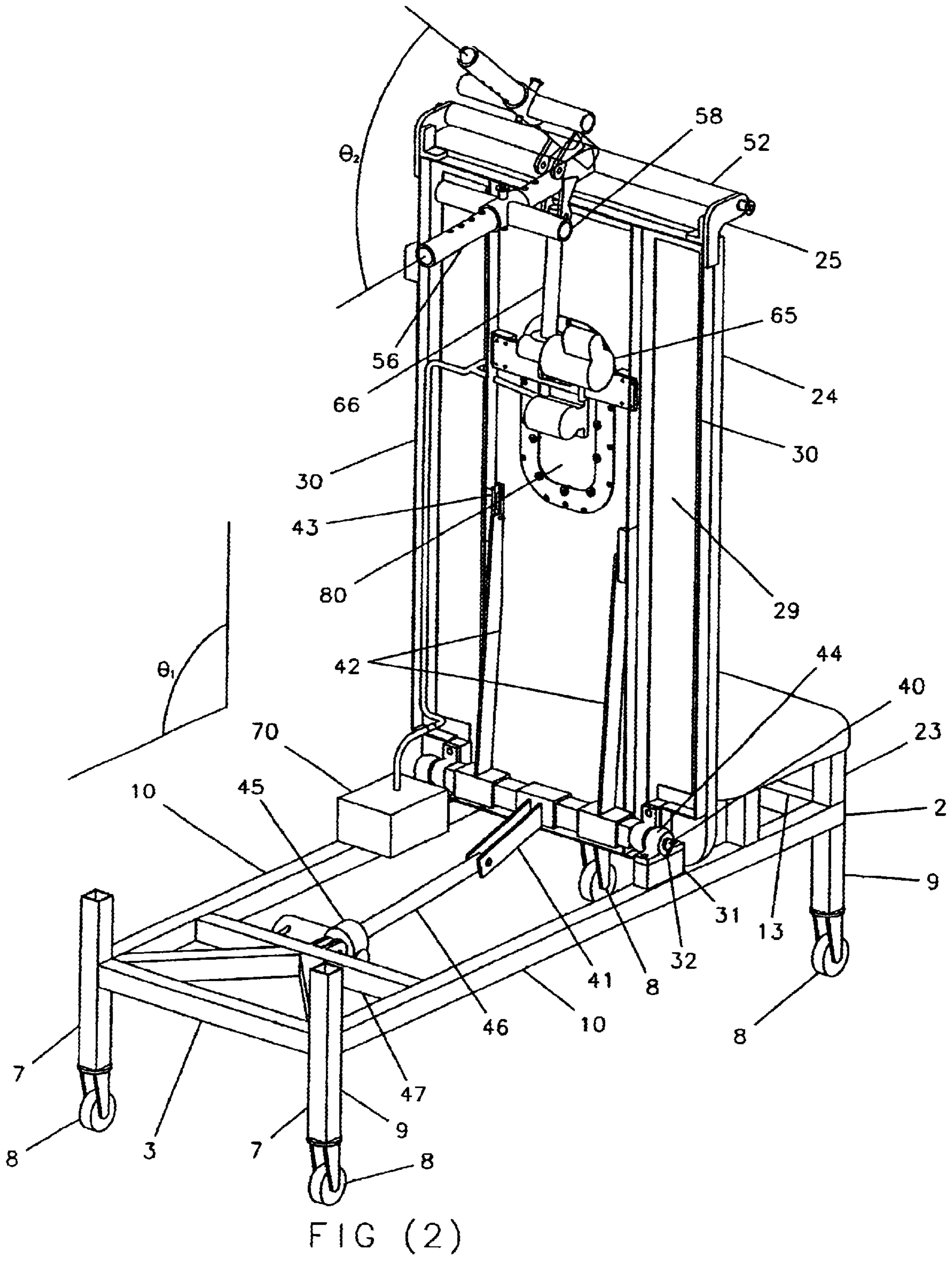
FIG (2)

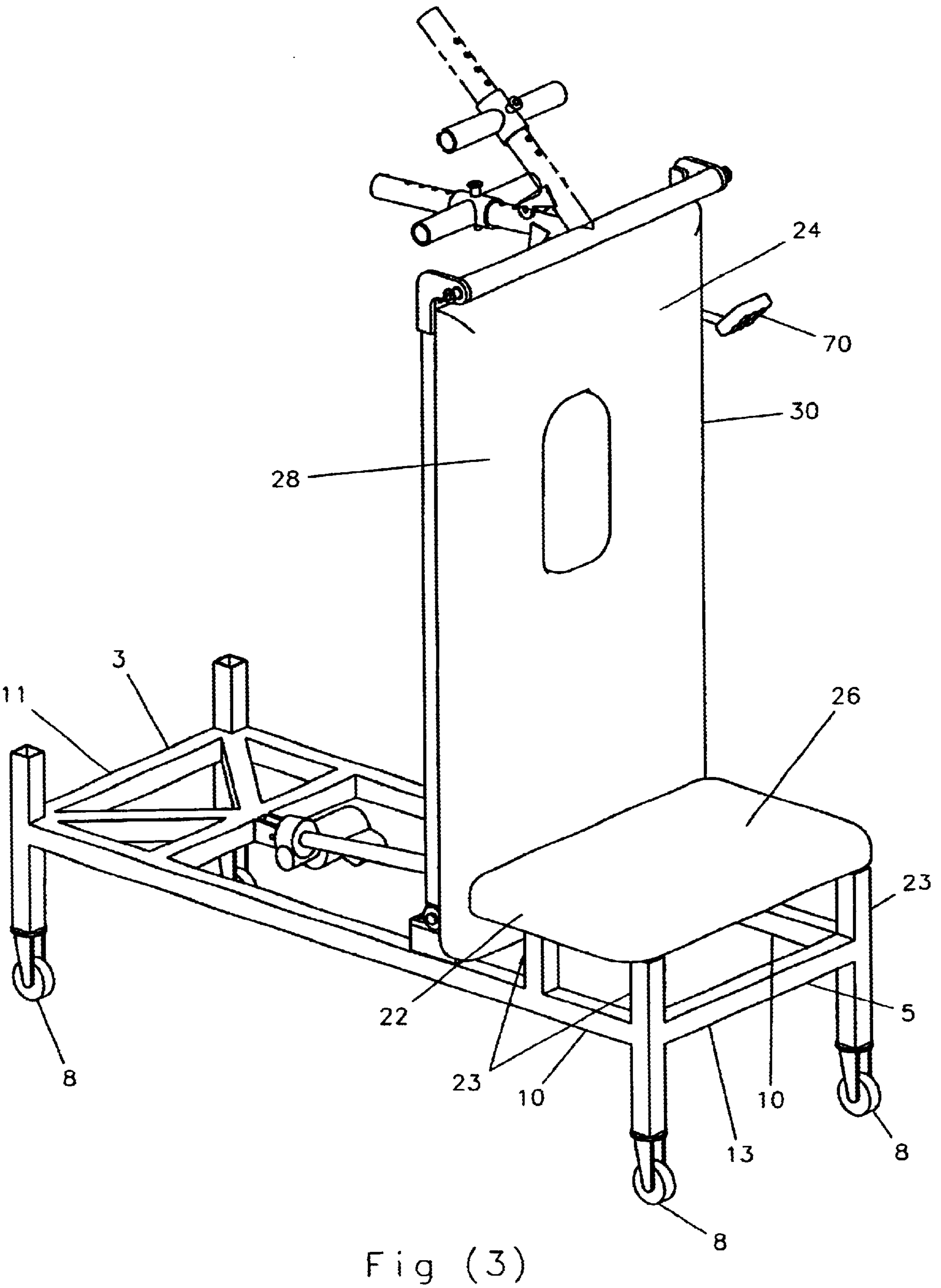
Fig (3)

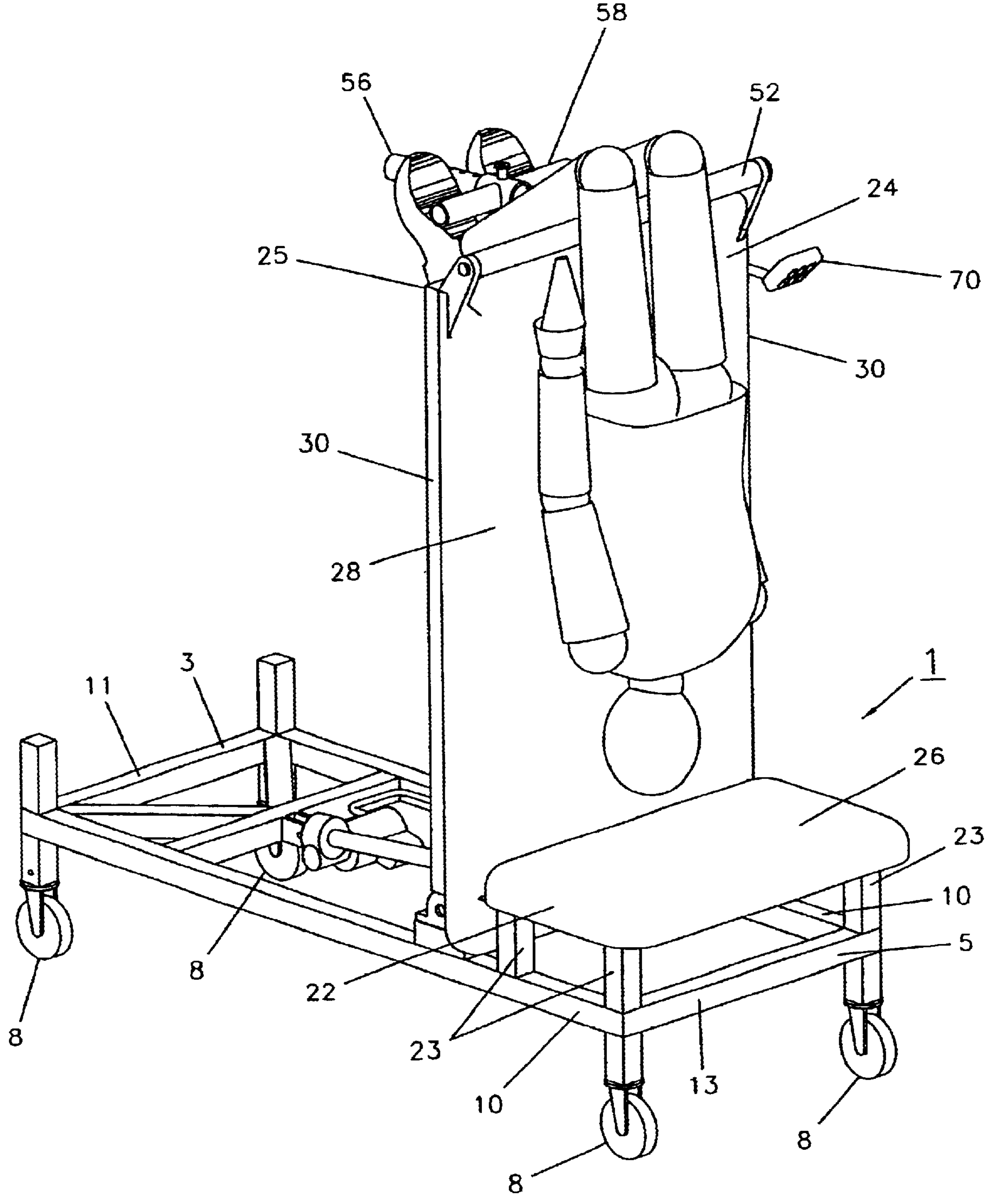
Figure (4)

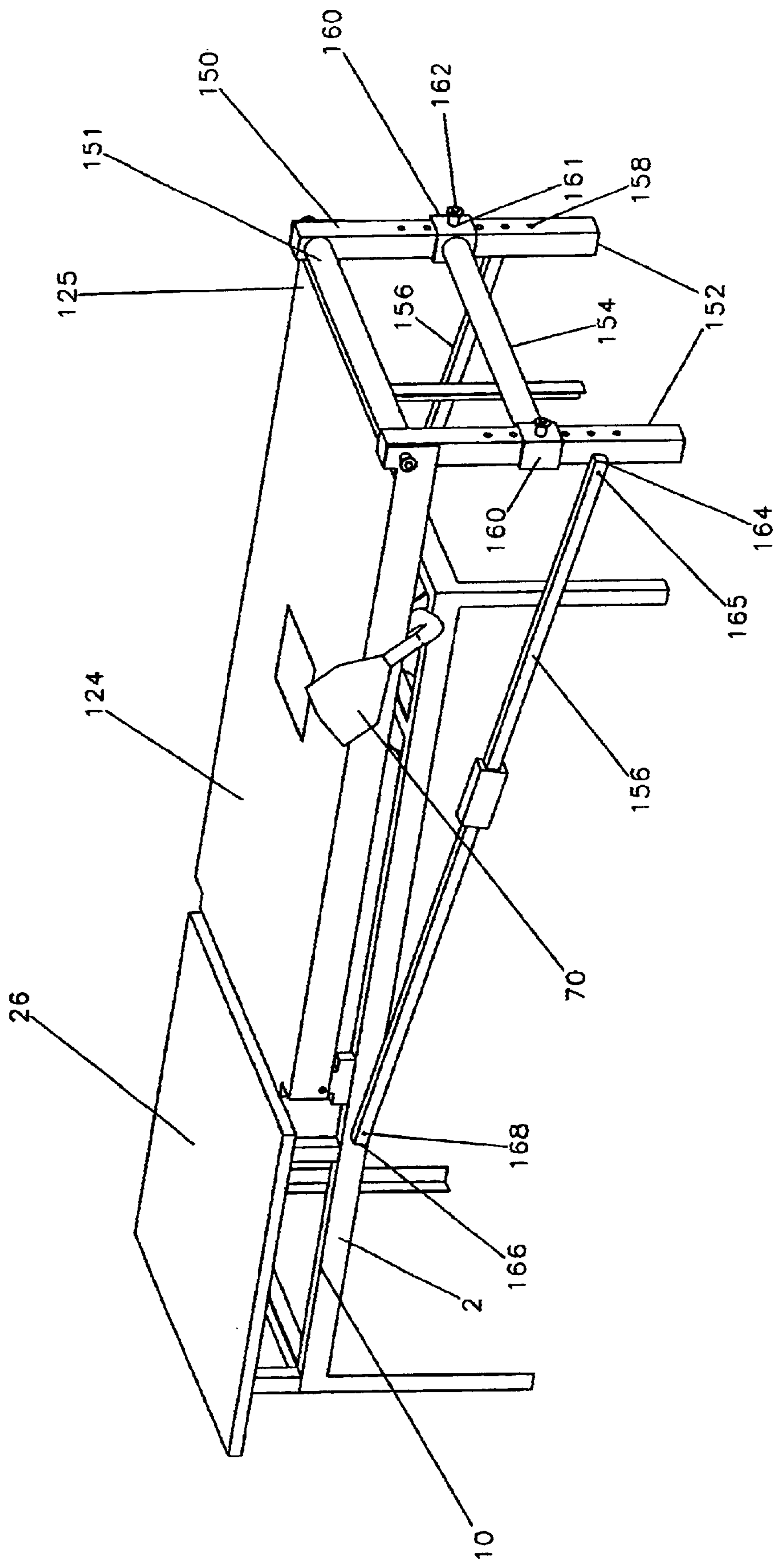
Figure (5)

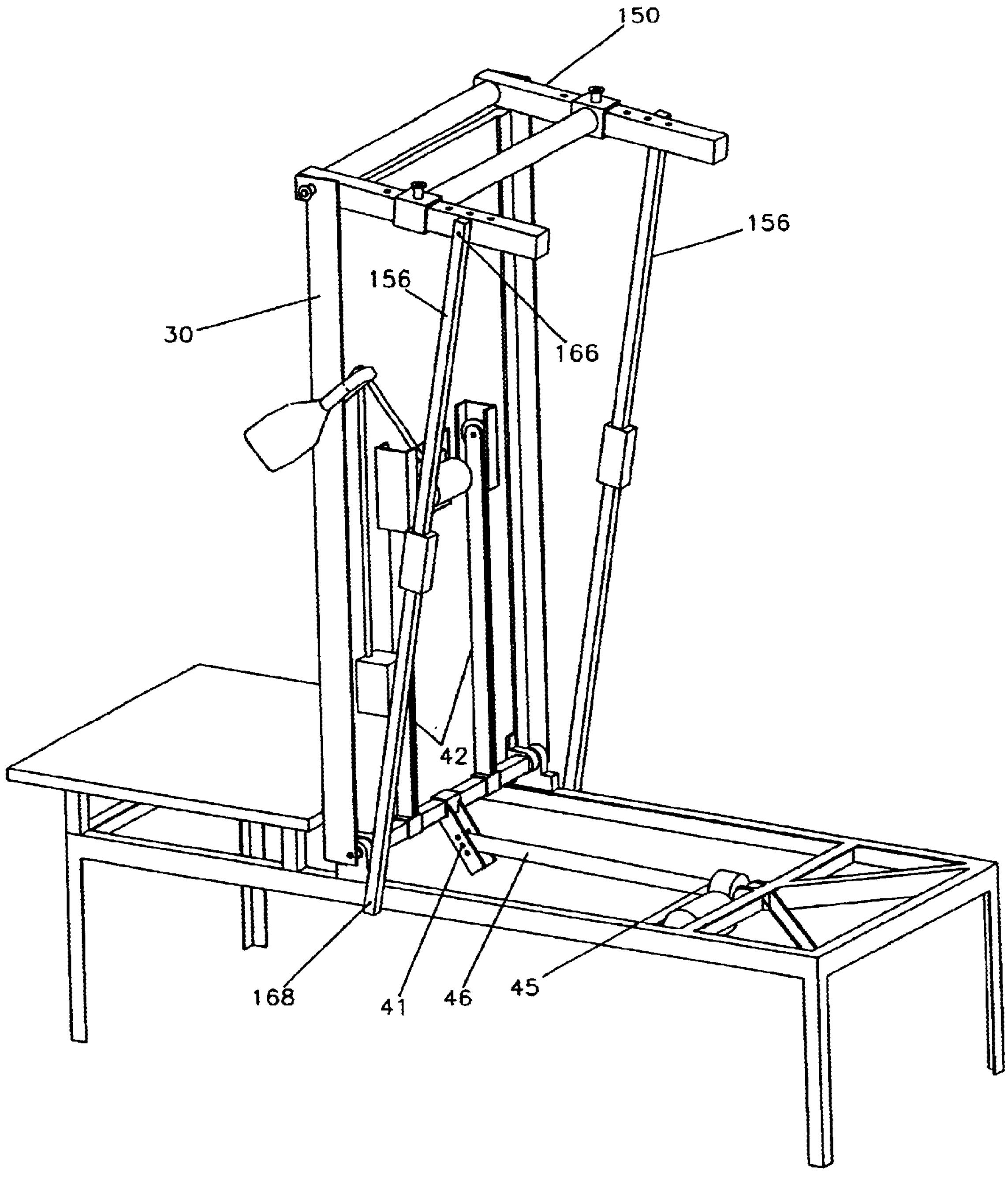
Figure (6)

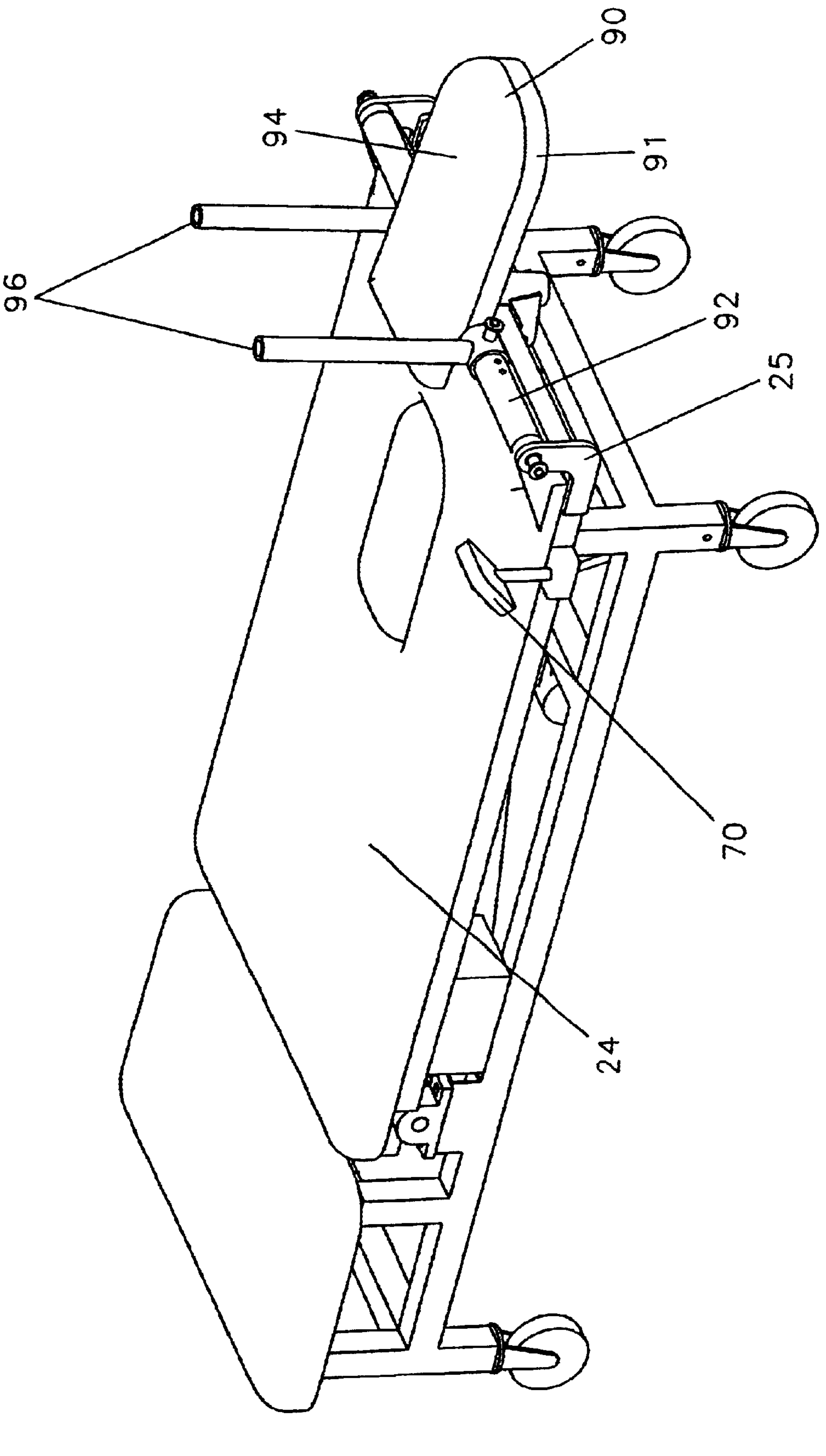
Figure (7)

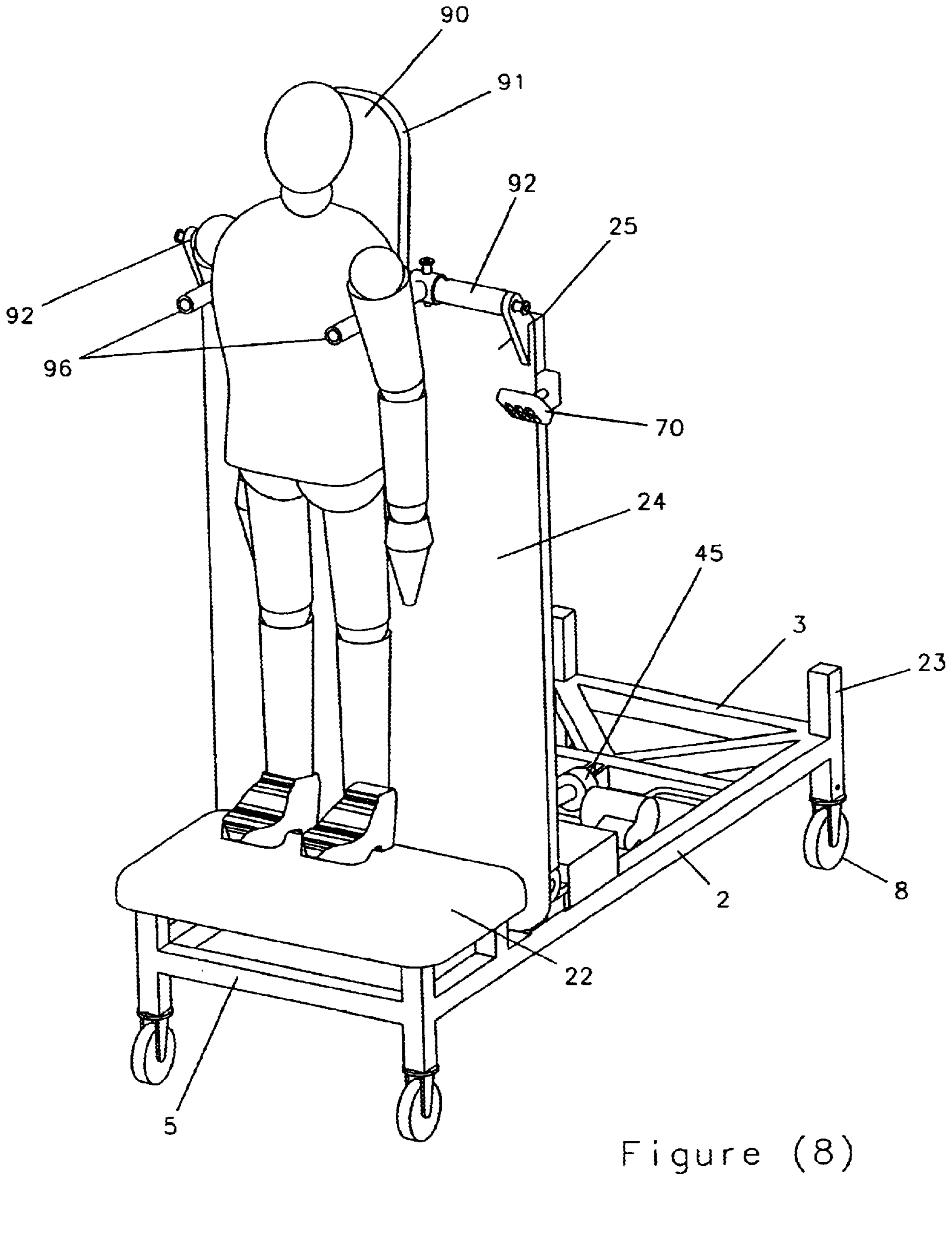
Figure (8)

YOGA INVERSION BED WITH LEG ATTACHMENT

This application claims the benefit of priority of U.S. patent provisional application Serial No. 60/382,338, filed in the United States Patent & Trademark Office on May 23, 2002.

FIELD OF INVENTION

The present invention relates to the field of devices which encourage and facilitate the practice of Yoga. More specifically, the present intention relates to a inversion bed having a leg attachment which facilitates the practice of "Monkey Swing Yoga".

BACKGROUND OF THE INVENTION

Yoga, as a body of exercises for promoting physical and mental well-being, has been practiced in various forms throughout the Indian subcontinent for several thousand years.

Today, schools offering a myriad of yoga disciplines currently exist that convey the teachings of yogis worldwide, especially in western countries, as interest in alternatives to western medicine are sought. Amongst the schools of yoga practiced two thousand years ago is "Monkey Swing Yoga" which has disappeared from practice, yet offers a stark contrast to the remaining yoga schools. As the name implies, the Monkey Swing Yoga includes yoga poses in which the practitioner swings in an inverted position, relieving compressive pressures on the chest, neck and spine, reversing the effects of gravity on the internal organs and strengthening the muscles of the abdomen and back. Importantly, the inverted swinging positions stimulate blood flow to the head and reduce blood pooling in the pelvic region and the legs. The practice of exercises of Monkey Swing Yoga are believed to calm the mind, thereby alleviating stress and mild forms of depression, as well as stimulating lungs, thyroid and digestive organs. In addition, it is believed that menopausal symptoms can be reduced, digestion can be improved and symptoms of anxiety, fatigue, headache, backache, insomnia, asthma, high blood pressure, osteoporosis and variscosities can be lessened.

Included among the poses assumed by more mainstream yoga schools are "Setu Bandha Sarvangasana", "Adho Mukha Svanasana" and "Halasana, Urdhva Dhanurasana" as well as headstands and shoulderstands. These poses are utilized to invert at least a portion of the body in recognition of the benefits achieved by such inversion. Attainment of these positions, as well as those of Monkey Swing Yoga, requiring good physical abilities, and may be difficult for injured, infirm or aged individuals. However, it is primarily such individuals who may benefit through the practice of this type of yoga.

Having parallel yet independent development in China beginning some 5,000 years ago, acupressure, acupuncture and reflexology also have received not only attention by western medical practitioners but also some acceptance as yet another form of alternative medicine. Both of these techniques focus on properly aligning the body's energy ("chi") along certain prescribed meridians along or through the chakra centers in similar fashion as kundalini based yoga methods. These techniques, when directed to the lower extremities are said to improve chi affecting improvements in the lymph system, the brain, sinuses, arm, neck, knees, stomach, abdominal organs, groin and genitalia. Moreover, directing pressure to the feet may address pathological conditions such as diabetes, hypothyroidism and the like.

A number of apparatus have been developed in the prior art to facilitate at least the partial inversion of the human body for therapeutic purposes. Such devices include tilting beds or boards which are designed to permit relaxation of the spine and to increase the strength of back muscles or to facilitate patient examinations. These type of devices are exemplified in U.S. Pat. No. 4,672,697, issued Jun. 16, 1987 to E. Schurch; U.S. Pat. No. 4,232,662, issued Nov. 11, 1980 to S. M. Barber; U.S. Pat. No. 3,806,109, issued Apr. 23, 1974 to A. Weber et al.; U.S. Pat. No. 4,739,749 to W. L. Lindley; U.S. Pat. No. 4,103,681, issued Aug. 1, 1978 to B. J. Shanley; U.S. Pat. No. 6,030,325, issued Feb. 29,2000 to B. Ottoson et al.; U.S. Pat. No. 5,133,741, issued Jul. 28, 1992 to P. L. Filho; U.S. Pat. No. 3,388,700, issued Jun. 18, 1968 to F. K. Mountz; U.S. Pat. No. 4,913,424, issued Apr. 3,1990 to R. A. Pepin; U.S. Pat. No. 6,243,897 to K. Sumiya; U.S. Pat. No. 5,416,939, issued May 23, 1995 to R. G. Maalouli; U.S. Pat. No. 5,334,123; issued Aug. 2,1994 to W. Rutherford; U.S. Pat. No. 4,438,761, issued Mar. 27,1984 to W. H. McGowen; U.S. Pat. No. 3,589,358, issued Jun. 29,1971 to J. J. Megal; U.S. Pat. No. 3,286,708, issued Nov. 22,1966 to R. Gartner; U.S. Pat. No. 3,081,085, issued Mar. 12, 1963 to R. de Giroland and U.S. Pat. No. 4,113,250, issued Sep. 12, 1978 to E. B. Davis.

Supportless therapeutic devices such as that shown in U.S. Pat. No. 3,593,708, issued Jul. 20, 1971 to V. Steele also have been developed. In addition, exercise equipment has incorporated body inversion, as disclosed in U.S. Pat. No. 5,885,197, issued Mar. 23, 1999 to J. Barton; U.S. Pat. Nos. 4,690,133 and 5,002,043, respectively issued Sep. 1, 1987 and Mar. 26, 1991 both to A. N. George; U.S. Pat. No. 5,935,050, issued Aug. 10, 1999 to E. L. Shahan; U.S. Pat. No. 6,309,330, issued Oct. 30, 2001 to T. L. Thornton; U.S. Pat. No. 4,461,287, issued Jul. 24, 1984 to H. Takahashi. Typically, the user of these devices is secured at the feet or thighs by the apparatus.

Despite the teachings of the prior art, an apparatus does not exist which combines both inverted yoga applications as well as those achieved through acupressure techniques.

SUMMARY OF THE INVENTION

Accordingly, it is an object of the present invention to provide an improved apparatus for inverting the human body to relax and exercise the spinal column, back muscles and stomach muscles.

It also is an object of the present invention to facilitate the practice of inverted yoga poses by applying a stretching force to the spine.

It is an additional object of the present invention to provide a an apparatus which allows for the controlled inversion of a patient, whether hale or injured through the provision of a pivotable bed which is motivated to the tilted position through the use of an electric actuator.

It is a further object of the present invention to provide an apparatus which permits the adjustable application of pressure to acupressure points while simultaneously providing means by which the yoga practitioner may hang or swinging the achievement of desired yoga poses and exercises.

Additional objects, advantages and novel features of the present invention will be set forth in part in the description which follows and in part will become apparent to those skilled in the art upon examination of the following specification or may be learned by practice of the invention. To the accomplishment of the above-related objects, this invention may be embodied in the forms illustrated in the accompanying drawings, attention being called to the fact, however, that the drawings merely are illustrative, and that changes may be made in the specific construction illustrated and described within the scope of the appended claims.

BRIEF DESCRIPTION OF THE DRAWINGS

The present invention will be better understood with reference to the appended drawing sheets, wherein:

FIG. 1 is a side perspective view of a first embodiment of the apparatus of the present invention.

FIG. 2 is a rear perspective view of a first embodiment of the present invention showing the apparatus in a position suitable for inverting a user.

FIG. 3 is a front perspective view of a first embodiment of the present invention showing the apparatus in a position suitable for inverting a user.

FIG. 4 is an environmental front perspective view of a first embodiment of the present invention showing the practitioner's engagement of the apparatus whilst in an inverted position.

FIG. 5 is side perspective view of a second embodiment of the present invention.

FIG. 6 is a side perspective view of a second embodiment of the present invention showing the apparatus in a position suitable for inverting a user.

FIG. 7 is a side perspective view of a first embodiment of the present invention with a chin-dip assist attachment attached thereto.

FIG. 8 is an environmental front perspective view of a first embodiment of the present invention showing an engagement of the apparatus by a user of the chin-dip assist attachment.

DETAILED DESCRIPTION

As shown in FIGS. 1, 2 and 3, the yoga apparatus 1 of the present invention comprises a rectangular base 2 having a front end 3, a rear end 5, a pair of front legs 7, a pair of rear legs 9, a pair of side members 10, a front end member 11 and a rear end member 13. Each of the pair of front legs and rear legs optionally may terminate with lockable casters 8 to permit rolling movement of the yoga apparatus so that it may be moved and positioned where desired. The rectangular base 2 is assembled with side members 10, front end member 11 and rear end member 13 forming a rectangular frame with the pairs of front and rear legs situated at its corners.

A bed 20, comprising a first padded board 22 having a top surface 26 and a bottom surface 27 and a second padded board 24 having a front end 25, a top surface 28, a bottom surface 29 and two opposing sides 30, is mounted to the rectangular base 2 in separate sections. The first padded board 22 is fixedly mounted above the rear end 5 of the base by vertical uprights 23 which also are fixedly mounted to the bottom surface 27 of the first padded board. To mount the second padded board 24 to the base 2, a pair of mounting brackets 31 is fixedly mounted to the base, each of the mounting brackets being mounted on respective opposing side members 10 and each being provided with a hole 32. An axle 40 having first and second ends is fixedly mounted to the bottom surface of the second padded board by tabbed "C" brackets 44; the axle is received and rotatably secured in the hole 32 of each of the mounting brackets 31 such that the axle is situated perpendicularly to the side members 10 and parallel to front end member 11 and the rear end member 13 of the base. A pair of lateral arms 42 is bolted at points along the length of the axle 40 and disposed perpendicular thereto. Securing means such as bolts 43 are used to fixedly join the pair of lateral arms 42 to bottom surface 29 of the second padded board 24 such that rotational force exerted on the axle may be translated to a lifting force through the lateral arms to the second padded board 24. A first actuator 45 is secured by mounting members 47 to the base 2 and functions to impart movement to a first piston 46 connected to a lever 41 fixedly attached to the axle 40, thereby rotating the axle. Translation of the rotation of the axle along the pair of lateral arms 42 results in a raising or lowering of the second padded board 24 through an angle $\theta_1$, wherein $\theta_1$, may be an angle of from 0 to about 90 degrees. Arbitrarily, a first position may be designated wherein $\theta_1$, equals 0 degrees and the second padded board 24 is parallel to the floor. Similarly, a second position may be designated wherein $\theta_1$=90 degrees and the second padded board 24 is perpendicular to the floor and, consequently, to the first padded board 22. By controlling the movement of the first actuator 45, the second padded board 24 may be pivoted and held at any intermediate position lying within the entire 90 degree range of $\theta_1$.

A leg attachment 50 is pivotally fixed to the front end 25 of the second padded board 24 and consists a leg attachment axle 52, a central bar 56 and a trapeze bar 58. The leg attachment axle 52 may be removably attached to the front end 25 of the padded board by any known fashion; for example, holes 55 may be provided near the front end of the padded board through which the ends of the leg attachment axle may be inserted. Holes for retaining securing pins may be provided in the axle ends so that the leg attachment axle may not be separated from the second padded board without the removal of the securing pins. The central bar 56 is fixedly attached to the center of the leg attachment axle by welding or other suitable means and is perpendicular thereto. Along the length of the central bar are several position holes 59 used in the positioning of the trapeze bar 58. The trapeze bar is movably mounted to the central bar, being perpendicular thereto and being provided with guide collar 60. By sliding the trapeze bar along the length of the central bar and by inserting a positioning pin 61 through a guide hole 62 in the guide collar 60 and into one of the position holes 59, the user may select a desired position for the trapeze bar. If desired, the trapeze bar may include padding that may be permanently or temporarily affixed to the surface of the trapeze bar.

A second actuator 65 is mounted to the bottom surface 29 of the second padded board 24 and imparts movement to a second piston 66 attached to the central bar member 56 of the leg attachment 50. Through the effects of this piston, the leg attachment may be pivoted through an angle $\theta_2$, where $\theta_2$, may be an angle of from 0 to about 90 degrees; as with the second padded board 24, the leg attachment may be moved and halted at any point within its range of movement. Thus, the leg attachment is capable of two types of movement: pivotal movement of the entire attachment imparted by the second actuator and linear movement of the trapeze bar 58 provided by a user. Electronic controls 70 are provided so that a user may control and coordinate the movements of both the second padded board 24 and the leg attachment 50.

To use the yoga apparatus 1, the yoga practitioner may lie down in a face up position on the bed 20, resting on the top surface 28 of the second padded board 24 and with the board in a first position parallel to the floor. Objects and other apparatus such as towels, oils, water bottles and the like may be stored on the top surface 26 of the first padded board 22. With the leg attachment 50 positioned at any desirable angle $\theta_2$, the yoga practitioner may insert his legs so that the top surface of his feet or his shins is in contact with the trapeze bar 58. By adjusting the positioning of the trapeze bar along the length of the central bar member 56, the practitioner may target desired acupressure points in the lower leg and foot regions. Manipulating the electronic controls 70 allows the user to elevate his body to an inverted position by raising the second padded board 24 through the actions of the first actuator from a horizontal position to a vertical position wherein $\theta_1$=90° and the practitioner is suspended in an inverted position as shown in FIG. 4. At any given angle $\theta_1$, and by similarly further manipulating the electronic controls, the practitioner may change the angle $\theta_2$ of the leg attachment 50 throughout its 90 degree range, thereby providing the yoga practitioner with a variety of poses with which to expound on a desired yoga pose.

While utilizing the apparatus for the purpose of achieving these poses, the pressure applied against the leg by the trapeze bar 58 simultaneously stimulates the range of acupressure points in the lower leg which it contacts. After performing the desired poses and exercises, the practitioner may proceed to use the electronic controls 70 to cause the return of the second padded board 22 to the horizontal position. The practitioner, by the control of the first and second actuators 45, 65 through the electronic controls is invested with complete control over the movement and positioning of both the second padded board and the leg attachment 50 and may stop or reverse the movements of either or both actuators depending on his convenience or need. Optionally, a heating and/or vibrating unit 80 may be embedded in or otherwise attached to the second padded board to provide further therapeutic stimuli to the user.

To augment the utility of the yoga apparatus 1, a chin dip assist attachment 90, well known in gyms and spas and shown in FIGS. 7 and 8, is provided for attachment to the front end 25 of the second padded board 24. The chin dip assist attachment comprises a rod 92 a headboard 94 and a pair of padded armrests 96. As with the leg attachment axle 52, the rod 92 may be inserted through holes 55 provided in the second padded board and may be secured thereto by the use of securing pins inserted into holes provided in the ends of the rod 92. The headboard is fixedly attached to the rod by any suitable means. Preferably, the headboard includes a head board frame 91 welded to the rod and being of a complementary shape to the head board. Bolts, adhesives and welding may be used to permanently affix the headboard to the headboard frame. Each of the padded armrests is removably attached to the rod, for example, by providing holes in the rods and complementary pins in the padded armrests. Preferably, the padded armrests may be removably attached to the rod at a plurality of positions so that they may be set at a variety of widths which are suitable for particular individuals.

In order to use the chin dip attachment, 90, the leg attachment 50 is removed from the yoga apparatus by disconnecting the second actuator 65 from the leg attachment, withdrawing the leg attachment axle 52 and replacing it with the rod 92. After arranging the armrests to a desired width, and with the second padded board 24 in the first position parallel to the floor, the user may situate himself so that the back of his head rests on the head board 94 and the palms of his hands, his elbows or arm pits rest upon the arm rests. Using the controls 70, the user may control the first actuator 45, rotating the second padded board upwardly until it attains a second position-perpendicular to the floor. In this position, the user will be in an upright, vertical position suspended by the palms, forearms or armpits whereat the user may assume various yoga positions or conduct reverse sit ups. Use of the apparatus may facilitate achieving these positions for users who are injured or otherwise invalided. When the user has completed his exercise regimen, he may use the controls to return the bed to the starting position.

A second embodiment of the present invention dispenses with the second actuator 45 while retaining some of the adjustment features of the leg attachment 50. Referring to FIGS. 5 and 6, the leg attachment 150 comprises a leg attachment axle 151, a pair of frame legs 152, a trapeze bar 154 and a pair of extendable bracing members 156. As with the leg attachment axle 52 of the previous embodiment, the leg attachment axle 151 is used to pivotally attach the leg attachment 150 to the front end 125 second padded board 124 as by providing holes in the front end through which the ends of the leg attachment axle may be inserted. The trapeze bar 154 terminates at each end with a mounting attachment 160 having a centered hole 161. Preferably each frame leg includes a plurality of holes 158; by sliding the respective mounting attachment over each of the frame legs, the bar may be positioned and retained thereon by inserting pins 162 through the centered hole 161 and into a desired respective hole 158 in each of the frame legs. Each of the bracing members 156 comprises a first end 164 and a second end 166. At a respective first end 164 of each of the bracing members 156 a simple bolt or screw 165 is used to pivotally attach the bracing member to a frame leg 152. In similar fashion, each of the bracing members is pivotally attached by another simple bolt or screw 168 at the second end 166 to a respective side member 10 of the rectangular base 2. By extending or contracting the extendable bracing members 156 the angle of the frame legs 152 may be adjusted to any position between a position wherein the leg attachment 150 is perpendicular to the second padded board 124 and a position wherein it is parallel thereto.

As with the first embodiment, a user may lie down in a face up position on the bed 20 while the second padded board 124 is located in a position parallel to the floor. The leg attachment is adjusted so that the frame legs 152 are at a desired angle and the trapeze bar 154 is at a desired position. The trapeze bar is secured with pins 162 and the bracing members are locked to the adjusted length so that the angle of the of the leg attachment 150 with respect to the second padded board 124 is fixed. The user engages the trapeze bar 154 in the same manner as for the first embodiment and electronic controls 70 are used to direct the movements of the first actuator 45. It is easily seen that the second embodiment, being a simplification of the first embodiment does not permit the range of fine control over the leg attachment that the first embodiment offers; however, it does still permit the user to adjust the angle at which his lower torso engages the apparatus during poses, simultaneously providing pressure to desirable acupressure points.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A bed for facilitating the inversion of a human body comprising:

a rectangular base having a front end, a rear end and opposing sides;

a first padded board fixedly mounted to said rear end of said rectangular base;

a second padded board having a first end proximal to said first padded board, a second distal end and opposing sides, said first end of said second padded board being pivotally secured to said rectangular base;

a leg attachment including an axle, a central bar and a trapeze bar, said leg attachment being removably secured to said second distal end of said second padded board by said axle, said central bar depending from said axle and said trapeze bar adapted to be slidably mounted on said central bar at a plurality of positions;

a first actuator, said first actuator being mounted to said rectangular base and having a first reciprocating piston, said first actuator providing a force through the movement of said first reciprocating piston to pivot said second padded board between a first position and a second position;

a second actuator, said second actuator being mounted to said second padded board and having a second reciprocating piston, said second actuator providing a force through the movement of said second reciprocating piston to pivot said leg attachment between a first leg position and a second leg position, and an electronic control device, said electronic control device adapted to control the activation of said first and second actuators.

2. A bed according to claim 1, wherein said first position of said second padded board is parallel to said rectangular base and said second position of said second padded board is perpendicular thereto.

3. A bed according to claim 1, wherein said first leg position of said leg attachment is parallel to said second padded board and said second leg position of said leg attachment is perpendicular thereto.

4. A bed according to claim 1, wherein said central bar depends from said axle and is perpendicular thereto.

5. A bed according to claim 4, wherein said trapeze bar is slidably mounted on said central bar and is perpendicular thereto.

6. A bed, according to claim 1, further comprising a chin dip assist attachment which may be removably secured to said second end of said second padded board when said leg attachment is removed therefrom.

7. A bed, according to claim 1, wherein said rectangular base further comprises four legs, each of said legs being positioned at the corners thereof.

8. A bed, according to claim 7, wherein said each of said legs is provided with a lockable caster whereby said bed is mobile.

9. A bed, according to claim 1, further comprising a heating unit, said electronic control device being adapted to control said heating unit.

10. A bed, according to claim 1, further comprising a vibrating unit, said electronic control device being adapted to control said vibrating unit.

11. A method for effecting an inversion of a user's body with a bed according to claim 1, said method comprising the steps of:

positioning a user supinately upon said second padded board with said second padded board being situated in a first position, wherein said first position is parallel to the floor;

positioning the user's legs such that said trapeze bar contacts the user's shins, with said leg attachment being in said first leg position, and manipulating said electronic control device to cause said first actuator to move said second padded board to said second position.

12. The method according to claim 11, said method further comprising the step of:

manipulating said electronic control device to cause said second actuator to move said leg attachment to a second leg position.

13. A method according to claim 12, wherein said second position of said second padded board is perpendicular to the floor, said method further comprising the steps of:

hanging by said trapeze bar for a predetermined period of time, and manipulating said electronic control device to cause said first actuator to move said second padded board to said first position.

14. A bed for facilitating the inversion of a human body comprising:

a rectangular base having a front end, a rear end and two opposing sides;

a first padded board fixedly mounted to said rear end of said rectangular base;

a second padded board having a first end proximal to said first padded board, a distal second end and opposing sides, said first end of said second padded board being pivotally secured to said rectangular base;

a leg attachment including an axle secured to said distal second end of said second padded board, two frame legs pivotally connected to opposing ends of said axle and a trapeze bar, said trapeze bar being slidably mounted to said two frame legs, said leg attachment being pivotable between first leg position and a second leg position;

a pair of bracing members each in the form of a rod having a first end and a second end and each of which being lockable to a fixed length, said first end of each of said bracing members being pivotally secured to a respective opposing side of said rectangular base, said second end of each of said bracing members being pivotally secured to a respective opposing frame leg of said leg attachment, wherein said bracing members when locked secure said leg attachment in either of said first leg position or said second leg position or any position therebetween;

an actuator, said actuator being mounted to said rectangular base and having a reciprocating piston, said actuator providing a force through the movement of said reciprocating piston to pivot said second padded board from a first position to a second position, and an electronic control device, said electronic control device adapted to control the activation of said first and second actuators.

15. A bed, according to claim 14, wherein said first position of said second padded board is parallel to said rectangular base and said second position of said second padded board is perpendicular thereto.

16. A bed, according to claim 14, wherein said first leg position of said leg attachment is parallel to said second padded board and said second leg position of said leg attachment is perpendicular thereto.

17. A bed, according to claim 14, wherein said trapeze bar is perpendicular to said opposing frame legs.

18. A bed, according to claim 14, wherein said rectangular base further comprises four legs, each of said legs being positioned at the corners thereof.

19. A bed, according to claim 14, further comprising a vibrating unit and a heating unit, said electronic control device being adapted to control said vibrating unit and said heating unit.

* * * * *